(12) United States Patent
Sakuma et al.

(10) Patent No.: US 7,250,453 B2
(45) Date of Patent: Jul. 31, 2007

(54) ANTI-BACTERIAL COMPOSITE PARTICLES AND ANTI-BACTERIAL RESIN COMPOSITION

(75) Inventors: Shuji Sakuma, Chuo-ku (JP); Tomoki Saito, Chuo-ku (JP); Yuki Sasaki, Minamiashigara (JP); Yasuo Matsumura, Minamiashigara (JP); Etsuo Tominaga, Minamiashigara (JP); Takayoshi Aoki, Minamiashigara (JP)

(73) Assignees: Kabushiki Kaisha Sangi, Tokyo (JP); Fuji Xerox Co., Ltd., Tokyo (JP)

( * ) Notice: Subject to any disclaimer, the term of this patent is extended or adjusted under 35 U.S.C. 154(b) by 43 days.

(21) Appl. No.: 10/492,352

(22) PCT Filed: Oct. 10, 2002

(86) PCT No.: PCT/JP02/10513

§ 371 (c)(1),
(2), (4) Date: May 6, 2004

(87) PCT Pub. No.: WO03/033596

PCT Pub. Date: Apr. 24, 2003

(65) Prior Publication Data

US 2004/0259973 A1      Dec. 23, 2004

(30) Foreign Application Priority Data

Oct. 17, 2001    (JP) .............................. 2001-319574

(51) Int. Cl.
C09D 5/16    (2006.01)

(52) U.S. Cl. ....................................... 523/122; 523/210

(58) Field of Classification Search ................ 523/122, 523/120
See application file for complete search history.

(56) References Cited

U.S. PATENT DOCUMENTS 4,250,277 A * 2/1981 Maries et al. ............... 525/337
4,906,464 A * 3/1990 Yamamoto et al. ......... 424/489
5,151,122 A    9/1992 Atsumi et al.
5,614,568 A * 3/1997 Mawatari et al. ........... 523/122
6,663,877 B1 * 12/2003 Appleton et al. ........... 424/411

FOREIGN PATENT DOCUMENTS

| EP | 0 427 858 A | 5/1991 |
|---|---|---|
| EP | 0 540 819 A | 9/1992 |
| EP | 0 540 011 A | 5/1993 |
| EP | 0 678 548 A | 10/1995 |
| EP | 1 442 659 A | 8/2004 |
| JP | 63-175117 | 7/1988 |
| JP | 63-54013 | 10/1988 |
| JP | 2-180270 | 7/1990 |
| JP | 3-218765 | 9/1991 |
| JP | 5-154 | 1/1993 |
| JP | 7-138416 | 5/1995 |
| JP | 10-219084 | 8/1998 |
| JP | 10-279818 | 10/1998 |
| JP | 11-335481 | 12/1999 |
| JP | 2000-128999 | 5/2000 |
| JP | 2000-212340 | 8/2000 |
| JP | 2001-139832 | 5/2001 |

* cited by examiner

*Primary Examiner*—Edward J. Cain
(74) *Attorney, Agent, or Firm*—Steptoe & Johnson LLP

(57) ABSTRACT

Anti-bacterial composite particles which comprise a polymer base material comprising a thermal melting polymer, such as a polyolefine, exhibiting good dispersibility in a basic material resin and having a lower molecular weight or a lower softening point than that of the basic material resin, and inorganic fine particles comprising a metal having anti-bacterial activity carried thereon. An antibacterial resin composition can be prepared by melting and kneading a synthetic resin composition as the basic material resin together with the anti-bacterial composite particles and forming by known molding methods such as extrusion molding and injection molding, and can be used for producing various synthetic resin moldings which have an inorganic anti-bacterial agent uniformly dispersed in a synthetic resin composition and thus exhibits good anti-bacterial effect.

20 Claims, No Drawings

ANTI-BACTERIAL COMPOSITE PARTICLES AND ANTI-BACTERIAL RESIN COMPOSITION

TECHNICAL FIELD

The present invention relates to antibacterial composite particles and an antibacterial resin composition, which have an antibacterial function.

BACKGROUND ART

In order to impart antibacterial activity to various kinds of synthetic resin molded articles, such as fibers and the like, it has been considered that a metal having antibacterial activity is added to a synthetic resin material. For example, there has been such a method in that a metal or metallic compound having antibacterial activity is added directly to a synthetic resin material. However, due to a significant difference in physical property between the metal or metallic compound and the synthetic resin material, the synthetic resin material is largely influenced thereby to restrict the range of utilization thereof, and furthermore, there is such a possibility that the metal or metallic compound is released from the synthetic resin molded article during use to cause influence on durability of the antibacterial activity and to cause unexpected adverse side effect with the metal or metallic compound thus released.

In order to solve the problem, JP-B-63-54013 and JP-A-63-175117 disclose that antibacterial zeolite obtained by carrying an antibacterial metal on zeolite by ion exchange is added to fibers or a fiber material.

JP-A-2-180270, JP-A-3-218765 and JP-A-5-154 disclose an antibacterial composition obtained by carrying an antibacterial metal and a metallic ion thereof on hydroxyapatite, which is most frequently used among calcium phosphate materials.

However, in the case where powder of the antibacterial zeolite or the antibacterial hydroxyapatite having an antibacterial metallic ion carried thereon is added directly to, for example, a raw material polymer for fibers, to prevent propagation of microorganisms, the zeolite or hydroxyapatite powder is liable to be aggregated among particles and is difficult to be dispersed, and therefore, the antibacterial agent is difficult to be present uniformly on the surface of fibers to fail to obtain good antibacterial activity. Accordingly, unevenness in quality of antibacterial activity is liable to occur when a small amount of the antibacterial agent is used.

In view of the above, it has been attempted upon mixing antibacterial ceramic powder with a raw material polymer for various kinds of synthetic resin molded articles that, as the first step, a master batch containing the antibacterial agent in a high concentration is prepared, and as the second step, the master batch is added to the raw material polymer for molded articles to obtain a prescribed concentration of the antibacterial agent, so as to attain uniform mixing.

In the case where the aforementioned production process is carried out, it is necessary that the master batch mixed with the antibacterial ceramic powder and the raw material polymer for molded articles are simultaneously melted. Therefore, it is preferred that the master batch has a melting point and physical property that are completely same as those of the raw material polymer for the synthetic resin composition constituting the molded articles. In order to satisfy the requirement, it is necessary that the base material of the master batch having the antibacterial agent mixed therein is the same as the polymer, and the particle diameter of the master batch is reduced.

However, in order to obtain a finely particulate master batch, it is necessary that the master batch having been once produced is pulverized by sufficiently cooled with a freezing medium and then subjected to some particular process steps, such as homogenization of the particle diameter and the like step, and therefore, it is disadvantageous in production time and cost. Furthermore, while it has been proposed that a polymer having a low melting point, such as polyolefin wax and the like, is used as the base material of the master batch, there is a significantly large difference in viscosity between the master batch base material and the basic material resin at the production temperature of molded articles, whereby the master batch suffers segregation to cause such a problem that it cannot be uniformly mixed in the basic material resin.

DISCLOSURE OF THE INVENTION

Under the circumstances, an object to be attained by the invention is to provide a simple and useful production technique with versatility capable of producing an antibacterial resin composition and an antibacterial resin product exerting excellent antibacterial activity with a small amount of an antibacterial agent by improving uniformity in dispersion of an inorganic antibacterial agent upon adding the antibacterial agent to various kinds of synthetic resin compositions, such as fibers and the like.

Another object thereof is to provide, by utilizing the technique, an antibacterial resin composition and an antibacterial resin product having sufficient antibacterial activity without impairing the inherent characteristics of the material.

It has been found that the objects can be attained by antibacterial composite particles, which are constituted by a polymer base material having a glass transition temperature within a certain range and showing a certain value of a melt viscosity at a certain temperature, and inorganic fine particles carrying a metal having antibacterial activity.

Accordingly, antibacterial composite particles, which are constituted by a thermoplastic polymer base material having a glass transition temperature of from 10 to 85° C. and a melt viscosity at 90° C. within a certain range and inorganic fine particles carrying a metal having antibacterial activity, are mixed and kneaded with a synthetic resin composition containing the base material, and the mixture is further subjected to the known molding method or spinning method, such as extrusion molding, injection molding and the like, to obtain various kinds of synthetic resin molded articles having good antibacterial activity and containing the inorganic antibacterial agent uniformly dispersed in the synthetic resin composition.

For example, antibacterial composite particles, which are obtained by adding and/or coating inorganic fine particles carrying a metal having antibacterial activity to a base material having affinity with a fiber forming polymer and having a glass transition temperature of from 10 to 85° C. and a melt viscosity at 90° C. of from $10^4$ to $10^6$ Pa·S, are mixed with the fiber forming polymer at an arbitrary stage until discharge of the fiber forming polymer from a spinning nozzle, followed by spinning, whereby fibers having sufficient antibacterial activity can be obtained without impairing the inherent characteristics of the material.

The invention will be described in detail below.

The inorganic fine particles used in the antibacterial composite particles of the invention will be described.

The inorganic fine particles are fine particles of an inorganic antibacterial agent formed by carrying a metallic element and/or a metallic ion having antibacterial activity (hereinafter, sometimes referred to as an antibacterial metal) on an inorganic ceramic carrier, and are not particularly limited as far as they are harmless to the human body.

Examples of the antibacterial metal contained in the inorganic antibacterial agent include at least one selected from the group consisting of silver, copper, zinc, gold, platinum and nickel under consideration of safety to the human body, and the use of silver, copper and zinc is most preferred among the antibacterial metals under consideration of fulfillment of high antibacterial activity, the productivity, the production cost and the like.

Examples of the carrier for carrying the antibacterial metal and metallic ion include at least one selected from the group consisting of a phosphate salt compound, such as calcium phosphate, zirconium phosphate and the like, alumina, silica, zeolite, calcium carbonate, calcium silicate, bentonite, titanium oxide and zinc oxide.

The aforementioned compounds, i.e., alumina, silica, zeolite, a phosphate salt compound, calcium carbonate, calcium silicate, bentonite, titanium oxide and zinc oxide, are harmless to the human body and excellent in capability to fixing the metallic element and/or the metallic ion. A single compound may be selected from the aforementioned carriers and used as a carrier, and plural compounds may be also selected therefrom and used as a carrier.

A phosphate salt compound is preferably selected as a carrier since it is such a compound that has high ion exchanging capability and exhibits a low elution amount of the antibacterial metal carried thereon. With respect to the mode of carrying the antibacterial metal on the carrier, the entire of the metallic ion may not be ion-exchanged, but it is considered that a part of the metal is retained by adsorption, and such a configuration is preferred from the standpoint of antibacterial activity.

Specific examples of the phosphate salt compound include at least one selected from the group consisting of a calcium phosphate compound, such as tricalcium phosphate ($Ca_3(PO_4)_2$), calcium hydrogen phosphate ($CaHPO_4$), hydroxyapatite ($Ca_{10}(PO_4)_6(OH)_2$), calcium hydrogen pyrophosphate ($CaH_2P_2O_7$), calcium pyrophosphate ($Ca_2P_2O_7$) and the like, a titanium phosphate compound, such as Ti ($HPO_4)_2$ and the like, a zirconium phosphate compound, such as $Zr(HPO_4)_2$ and the like, a magnesium phosphate compound, such as $Mg_3(PO_4)_2$ and the like, an aluminum phosphate compound, such as $AlPO_4$, a manganese phosphate compound, such as $Mn_3(PO_4)_2$ and the like, and an iron phosphate compound, such as $Fe_3(PO_4)_2$ and the like. The antibacterial agent using these phosphate salt compound as a carrier exhibits a low elution amount of the metallic ion (desorption) and high durability in antibacterial activity.

The carrier may be either a natural product or a synthetic product, and is preferably a synthetic product since particles having uniform quality can be obtained. Those having various kinds of crystallinity are obtained depending on the production process, for example, an amorphous carrier can be produced by synthesizing a phosphate salt by the wet method using a solution reaction, and a carrier having high crystallinity can be obtained by carrying out a baking process, and all of them may be used. The phosphate salt may contain crystal water.

Among the phosphate salt compounds, a calcium phosphate compound is most preferably used since it has good affinity to the human body (biocompatibility), high durability in antibacterial activity and excellent safety. The calcium phosphate compound may be, in addition to those described in the foregoing, halogenated apatite $Ca_{10}(PO_4)_6X_2$ (wherein X represents F or Cl) or a nonstoichiometric apatite $Ca_{10-z}(HPO_4)_y(PO_4)_{6-y}X_{2-y-z}H_2O$ (wherein X represents OH, F or Cl, and y and z represent a nonstoichiometric ratio).

The inorganic antibacterial agent used in the antibacterial composite particles of the invention preferably contains the aforementioned compound as the carrier, preferably a phosphate salt compound, and particularly a calcium phosphate compound, selected as a carrier, and the inorganic antibacterial agent is preferably obtained by carrying at least one antibacterial metal selected from the aforementioned antibacterial metal, particularly silver, copper and zinc, on the carrier.

Examples of a method for carrying the antibacterial metal on the carrier include a method of carrying the metallic element and/or the metallic ion by adsorption, a method of carrying by an ion exchange reaction, a method of carrying by a mechanochemical reaction, and the like reactions, and the inorganic antibacterial agent containing the carrier formed of an inorganic compound having the antibacterial metal carried thereon can be prepared by these methods.

The mechanochemical reaction is such a method that a slurry of an antibacterial agent having a uniform particle diameter is produced from the starting substances through adsorption and/or ion exchange by using a mixing apparatus, such as a ball mill and the like. For example, starting substances for producing the carrier (a calcium compound, such as calcium carbonate and the like, and phosphoric acid or the like) and an aqueous solution of the antibacterial metal are placed in a ball mill, and the ball mill is driven for a prescribed period of time, whereby zirconia balls in the ball mill agitate the slurry of the starting substances and simultaneously pulverize the reaction product. The reaction of the starting substances and pulverization of the reaction product are simultaneously carried out by effecting the mechanochemical reaction for a prescribed period of time, and therefore, an antibacterial agent having uniform quality and a uniform particle diameter can be obtained, which is particularly preferred for mass production.

As the inorganic antibacterial agent, the aforementioned antibacterial metal is preferably carried on the carrier in an amount of from 0.05 to 30.0% by weight. In the case where the carried amount of the antibacterial metal is less than 0.05% by weight, the antibacterial activity is low, and there may be a case where a large amount of the antibacterial agent is necessarily used. In the case where the antibacterial agent is carried in a carried amount exceeding 30.0% by weight, on the other hand, the antibacterial agent is liable to be released due to weak bond between a part of the antibacterial agent and the carrier, so as to bring about such a tendency that the resin molded article is liable to be colored.

The antibacterial composite particles of the invention may contain other inorganic compounds, such as silicon dioxide, zinc oxide and the like, for other purposes in such an amount that does not impair the objects of the invention, in addition to the inorganic compound as the carrier and the antibacterial metal. For example, silicon dioxide has an effect of improving whiteness of the antibacterial agent, and zinc oxide has an effect of improving the antibacterial spectrum of the antibacterial agent (i.e., the number of bacterial strains as a target, to which the antibacterial activity is effected, is increased), with both of the inorganic compounds being harmless to the human body. In this case, the target of the antibacterial activity is broadened when silver is particularly used as the antibacterial metal, and copper also exerts antifungal activity.

The inorganic antibacterial agent using a phosphate salt compound as a carrier is preferably subjected to a baking treatment at from 500 to 1,200° C. The inorganic antibacterial agent having been subjected to the baking treatment exhibits a significantly low elution ratio of the antibacterial metal in comparison to that have not been baked, and the durability (persistence) of the antibacterial activity is further excellent, whereby the storage stability of the product is improved. Accordingly, a phosphate salt compound having been subjected to a baking treatment is preferably used.

The addition amount of the inorganic antibacterial agent is preferably adjusted to from 0.01 to 10% by weight based on the weight of the basic material resin, and more preferably from 0.1 to 5.0% by weight. While it depends on the amount of the antibacterial metal carried on the inorganic carrier, in the case where the inorganic antibacterial agent having the antibacterial metal carried in an amount of 30.0% by weight is used, an addition amount of the inorganic antibacterial agent of less than 0.01% by weight brings about, for example, insufficient antibacterial activity imparted to fibers, and in particular, poor durability in antibacterial activity.

In the case where it exceeds 10% by weight, on the other hand, sufficient antibacterial activity is obtained, but for example, the proportion occupied by the inorganic antibacterial agent becomes too large in the polymer flow upon spinning fibers, and therefore, it is not preferred since such a problem occurs that the strength and the durability of the fibers are lowered.

The antibacterial agent is contained in a particulate polymer base material described later, and the content thereof is in a range of from 0.1 to 60% by weight based on the polymer base material. A too small content brings about poor antibacterial activity, and a too large content fails to attain further improvement in antibacterial activity of the final product.

The following polymer material is used as the polymer base material (hereinafter, sometimes referred to as a "core base material") constituting the antibacterial composite particles, whereby in the case where it is melted and mixed with a synthetic resin composition as the base material, the core base material is quickly melted and is melted and mixed with the base material, and as a result, the inorganic antibacterial agent is uniformly dispersed in the synthetic resin composition in a molten state. The synthetic resin product according to the invention uniformly contains the inorganic antibacterial agent to exert sufficient antibacterial activity without impairing the inherent characteristics of the material.

The core material has a glass transition temperature of from 10 to 85° C. and a melt viscosity satisfying the following equation:

$$10_4 Pa \cdot S \leq \eta^*(90° C.) \leq 10^6 Pa \cdot S$$

wherein $\eta^*$ represents a complex viscosity.

The complex viscosity referred in the invention is dynamic viscoelastic characteristics by the sine wave oscillation method under an oscillation frequency of 1 rad/sec. For example, it is measured with the ARES measuring device produced by Rheometric Scientific, Inc. Specific measuring conditions include the following conditions. After molding the powder to be measured into a tablet, it is set on parallel plates, and after setting the normal force to zero, sine wave oscillation is applied thereto at an oscillation frequency of 1 rad/sec. After retaining at a prescribed temperature for 20 minutes, the measurement is effected. It is preferred that the temperature adjustment range after starting the measurement is ±1.0° C. from the standpoint of fulfillment of measurement accuracy. During the measurement, the distortion amount is suitably retained at the respective measuring temperatures, whereby appropriate adjustment is attained to obtain pertinent measured values.

In general, the basic material resin is mixed with various kinds of additives in a molten state at a high temperature, and is molded into a molded article, fibers, films or the like through a cooling step. The melting temperature upon mixing is generally about from 150 to 400° C., and upon molding, the mold temperature is about from 10 to 180° C. Accordingly, it is demanded that the additives, such as the antibacterial agent and the like, are uniformly dispersed in the basic material resin upon melting, and maintains the dispersed state without maldistribution or aggregation even through the cooling step. Furthermore, it is preferred that the antibacterial agent is present on the surface of the resin because the antibacterial activity is exerted by the inorganic antibacterial agent present on the surface of the molded article.

In the case where the glass transition temperature of the polymer base material is less than 10° C., the difference in viscoelasticity from the basic material resin at the melt mixing temperature becomes too large, and therefore, there is a case where the uniform mixed state cannot be obtained.

In the case where the glass transition temperature exceeds 85° C., on the other hand, the compatibility with the resin is deteriorated due to the high viscosity upon melting, and therefore, effective mixing cannot be conducted upon melting. The glass transition temperature is preferably from 30 to 85° C., and most preferably from 40 to 80° C.

Furthermore, it is necessary that the following equation is satisfied:

$$10^4 Pa \cdot S \leq \eta^*(90° C.) \leq 10^6 Pa \cdot S$$

wherein $\eta^*$ represents a complex viscosity.

It has been known that a polymer base material having a viscosity in the aforementioned range exhibits significantly good dispersion upon melting, and a molded article has high antibacterial activity. It is considered that this is because upon cooling the basic material resin in a molten state, the antibacterial agent migrates to the vicinity of the surface owing to the suitable viscosity at that temperature.

In the case where the complex viscosity at 90° C. is $10^4$ Pa·S or less, the polymer base material suffers bleeding phenomenon at the molding or cooling step due to the too low viscosity thereof, whereby there is such a possibility that the antibacterial agent is reaggregated or aggregated on the surface of the resin, so as to induce deterioration of the characteristics of the basic material resin. In the case where the complex viscosity is $10^6$ Pa·S or more, the migration of the antibacterial agent to the surface does not occur due to the high viscosity, so as to fail to exert effective antibacterial activity.

In order to control the glass transition temperature within the aforementioned range, it can be lowered by selecting the species of the monomer and by using that having a long chain alkyl group. In general, the glass transition temperature can be lowered by lowering the molecular weight of the polymer.

The viscosity to be controlled within the aforementioned range can be controlled by changing the species of the monomer, the molecular weight and the extent of crosslinking, as similar to the control of the glass transition temperature. In the case of a polymer obtained by combining a high molecular weight component and a low molecular weight component, particularly, the low molecular weight component dominates the viscosity in a low temperature region, and the high molecular weight component dominates the viscosity in a high temperature region.

Furthermore, it is preferred that the melt viscosity satisfies the following equation:

$$10^3 Pa \cdot S \leq \eta^*(100° C.) \leq 10^5 Pa \cdot S$$

wherein $\eta^*$ represents a complex viscosity.

In the case where the melt viscosity at 100° C. is controlled within a range of from $10^3$ to $10^5$ Pa·S, an appropriate viscosity can be attained, whereby uniformity in dispersion is further improved, and exposure of the antibacterial agent on the surface can be further uniform.

Moreover, it is preferred to use a resin having a melt viscosity satisfying the following equation:

$$10^0 Pa \cdot S \leq \eta^*(180° C.) \leq 10^3 Pa \cdot S$$

wherein $\eta^*$ represents a complex viscosity.

By using the aforementioned range, melt mixing with the basic material resin can be smoothly carried out.

The softening point of the polymer base material is preferably lower than the softening point of the basic material resin by 20° C. or more. Owing to the appropriate difference in softening point, the basic material resin is melted after starting melting of the polymer base material, whereby a more uniform antibacterial resin can be obtained.

The softening point of the polymer base material is preferably from 50 to 150° C. It is more preferably from 70 to 150° C. The softening point of the polymer is determined by the flow tester method, and the temperature providing an apparent complex viscosity of $10^4$ Pa·S is designated as the softening point. Owing to the aforementioned softening point, bleeding is suppressed to attain higher antibacterial activity.

The molecular weight of the polymer basic material resin is preferably from 1,000 to 100,000 in terms of weight average molecular weight from the standpoint of control of the viscosity. It is more preferably from 2,000 to 50,000.

As the polymer base material, a crystalline polymer, a non-crystalline polymer and a non-crystalline polymer having a surface having been crystallized may be used. The thermoplastic resin used in the polymer base material is not particularly limited and may be appropriately selected. Examples thereof include single materials of polyester, polyamide, styrene, vinyl, acryl, epoxy, urethane, silicone, fluorine or cellulose resins, a resin derived therefrom and the like. In particular, polyester, polyamide, polystyrene and polyolefin series are preferred under consideration of easiness in mixing the inorganic antibacterial particles, dispersibility and versatility. Among these, a polyester resin is most preferably used.

Examples of the polystyrene include styrene, p-chlorostyrene, α-methylstyrene, a styrene copolymer, such as a styrene-butadiene copolymer, a styrene-isoprene copolymer, a styrene-maleic acid copolymer and the like, and the like.

The polyester is not particularly limited as far as it is polyester obtained through polycondensation of an alcohol component and a carboxylic acid component. Examples of the alcohol component include a divalent or more alcohol, an alcohol derivative, and the like, such as ethylene glycol, diethylene glycol, triethylene glycol, polyethylene glycol, propylene glycol, butanediol, pentanediol, hexanediol, cyclohexanedimethanol, xylylene glycol, dipropylene glycol, polypropylene glycol, bisphenol A, hydrogenated bisphenol A, bisphenol A ethylene oxide, bisphenol A propylene oxide, sorbitol, glycerin and the like. Examples of the carboxylic acid component include a divalent or more carboxylic acid, a carboxylic acid derivative, a carboxylic anhydride and the like, such as maleic acid, fumaric acid, phthalic acid, isophthalic acid, terephthalic acid, succinic acid, adipic acid, trimelliticacid, pyromelliticacid, cyclopentane dicarboxylic acid, succinic anhydride, trimellitic anhydride, maleic anhydride, dodecenyl succinic anhydride and the like. Two or more kinds of each of the alcohol component and the carboxylic acid component may be used in combination.

Specific examples include polyethylene terephthalate, polybutylene terephthalate, poly(ethylene terephthalate-isophthalate), poly(ethylene glycol-cyclohexanedimethanol-terephthalate), polycarbonate, polyallylate and the like.

Specific examples of the polyamide include nylon 4, nylon 6, nylon 12, nylon 66 and nylon 610.

Specific examples of the polyolefin include polyethylene, polypropylene, polybutene, butadiene and the like.

Other examples include an acrylate polymer, such as polymethyl acrylate, polyethyl acrylate, polybutyl acrylate, poly-2-ethylhexyl acrylate, polylauryl acrylate and the like, a methacrylate polymer, such as polymethyl methacrylate, polybutyl methacrylate, polyhexyl methacrylate, poly-2-ethylhexyl methacrylate, polylauryl methacrylate and the like, a copolymer of an acrylate and a methacrylate, a copolymer of a styrene monomer and an acrylate or a methacrylate, polyvinyl acetate, polyvinyl propionate, polyvinyl butyrate, an ethylenic polymer, such as polyethylene, polypropylene and the like, and a copolymer thereof, polyvinyl ether, polyvinyl ketone, polyurethane, a rubber material, an epoxy resin, polyvinyl butyral, rosin, modified rosin, a terpene resin, a phenol resin and the like, which may be used singly or as a mixture.

The basic material resin mixed in the composite particles is not particularly limited, and examples thereof include a synthetic resin and a semisynthetic resin, such as polyamide, such as nylon 6, nylon 66 and the like, a polyester resin, such as polyethylene terephthalate, polybutylene terephthalate, polycarbonate, polyarylate and the like, polyolefin, such as polyethylene, polypropylene, polymethylterpene, polybutene and the like, an acrylic resin, such as an acrylonitrile-butadiene-styrene (ABS) resin, an acrylonitrile-styrene (AS) resin, a methacrylic resin and the like, acrylonitrile, polyvinyl alcohol, a polystyrene resin, a butadiene resin, a polyvinyl chloride resin, a polyvinyl acetate resin, a polyacetal resin, a melamine resin, an epoxy resin, a urethane resin, a phenol resin, a fluorine resin and the like, copolymers thereof and the like. Particularly preferred resins among these include a styrene resin, an acrylic resin, an olefin resin and copolymers thereof.

For example, the effect can be particularly exerted in the case of the following combinations of the polymer base material and the basic material resin. The combination of polymer base material/basic material resin includes polyester/polyester, polyester/polyolefin, polyester/polyamide, polyester/acryl, polyolefin/polyolefin, polyamide/polyamide, acryl/styrene, acryl/acryl, styrene/acryl, styrene/styrene and the like. These resins may have any mode of a homopolymer, a copolymer, a mixture and the like.

The using proportion of the antibacterial composite particles may vary depending on the species of the basic material resin and the species of the core base material, and in general, the using amount of the core base material is preferably from 0.1 to 60% by weight based on the mass of the basic material resin, and more preferably about from 0.5 to 20% by weight. In the case where the using amount of the core base material is less than 0.1% by weight, dispersion of the antibacterial agent in the basic material resin becomes insufficient to lower the antibacterial activity of the product and the antibacterial resin composition itself. In the case where it exceeds 60% by weight, on the other hand, the productivity upon forming fibers is deteriorated to cause breakage of filaments, and there are such possibilities that the strength of the fibers thus obtained is lowered, and the inherent characteristics of the fibers cannot be exerted.

The method of adding the antibacterial composite particles to the basic material resin is preferably such a method that they are added to the basic material resin after completing polymerization under consideration of influence of those components on the polymerization reaction.

In the invention, therefore, it is preferred to employ a method of adding the antibacterial composite particles at a step, such as a step immediately after polymerization of the polymer constituting the basic material resin, a step of melting and mixing for producing pellets, chips or a molded articles from the polymerized resin composition, an arbitrary step until the polymer is spun with a spinning nozzle upon spinning for producing antibacterial fibers, and the like steps.

As described in the foregoing, the objects of the invention are attained by using the antibacterial composite particles as an essential component, and the antibacterial composite particles can be obtained by containing and/or coating the inorganic fine particles to the core base material.

As a method for obtaining the antibacterial composite particles of the invention, such a method can be employed that the inorganic fine particles are coated on the core base material by a mechanical method. In alternative, they can be produced by utilizing a method where a mixture obtained by melt mixing the inorganic fine particles with the molten thermoplastic resin is pulverized to a prescribed particle diameter, or a method of emulsion polymerization, suspension polymerization or the like of a mixture obtained by adding fine particles of the calcium phosphate antibacterial agent to the monomer component of the resin.

The mechanical method is such a method that the inorganic fine particles and the core base material are placed in a high speed gas flow mixer or a pulverizer, such as a Henschel mixer, hybridizer, an ong mill, Mechanofusion, Coatmizer, Dispercoat, Jetmizer and the like, and the inorganic fine particles are coated on the core base material at a rotation number of from 500 to 10,000 rpm, for from 1 to 120 minutes, and under temperature conditions where the temperature inside the apparatus is equal to or less than the softening temperature of the core base material.

The volume average particle diameter of the antibacterial composite particles thus obtained as having been described may be arbitrarily selected and is not particularly limited, and those of from 1 to 2,000 µm are practically useful, with from 100 to 1,000 µm being preferred. The production of polymer particles having a particle diameter less than 1 µm is disadvantageous from the standpoint of cost, and it is not preferred since significant improvement in effect cannot be expected. The particle diameter of the antibacterial composite particles can be selected from the aforementioned range depending on the purpose thereof, and in the case where those having a relatively small particle diameter are used, they can be uniformly dispersed in the resin composition, and in addition, the content of the antibacterial metal component in the resin composition can be increased, whereby high antibacterial activity can be obtained with a small addition amount. Furthermore, the release of the antibacterial metal component can be controlled by the carrying state of the antibacterial metal component on the polymer constituting the core base material (for example, a polymer having functional groups different in coordination property to the antibacterial metal component is used in the core base material) and the circumferential environment of the antibacterial metal component (hydrophilicity or hydrophobicity of the polymer), so as to obtain an instantaneous or persistent antibacterial agent.

Accordingly, the core base material used has a volume average particle diameter of from 1 to 2,000 µm. The shape of the core base material is not particularly limited, and may be various shapes, such as a spherical shape, an acicular shape, a spindle shape, a bar shape, a cylindrical shape, a polyhedral shape, a polyacicular shape and the like. In the case where the particle diameter of the core base material is increased, the velocity of the gas flow in the mixer is lowered, whereby the coating of the inorganic fine particles becomes non-uniform.

The volume average particle diameter of the inorganic fine particles coated on the surface of the core base material is equal to or less than the average particle diameter of the core base material upon use, and is preferably such a size that does not exceeds 10 µm, and more preferably 1 µm or less.

In the case where the particle diameter of the inorganic fine particles is larger than the particle diameter of the core base material, the antibacterial composite particles of the invention are difficult to be produced while a part of the inorganic fine particles is pulverized. Furthermore, in the case where the volume average particle diameter of the inorganic fine particles exceeds 10 µm, upon producing antibacterial fiber, for example, breakage of filaments or the like occurs upon spinning to deteriorate processability upon spinning.

In the invention, other additives that are generally used in a resin composition as a raw material of various kinds of resin products, such as an ultraviolet ray absorbent, an antistatic agent, an antioxidant, a lubricating agent, a fire retardant, a pigment, a plasticizer and the like, may be used depending on necessity, in addition to the aforementioned inorganic antibacterial agent.

In addition to the aforementioned mechanical method, the antibacterial composite particles of the invention can be produced by such a method that the thermoplastic resin used as a raw material of the core base material is mixed with the inorganic fine particles and melted and mixed to produce a mixture, which is then pulverized to the prescribed particle diameter by a mechanical method or the like.

It is considered that it is suitable that the thermoplastic resin and the inorganic fine particles are mixed by using a known mixer, such as a V blender, a Henschel mixer, a super mixer, a ribbon blender and the like, before melt mixing. At this time, in addition to the aforementioned inorganic antibacterial agent, other additives that are generally used in a resin composition as a raw material of various kinds of resin products, such as an ultraviolet ray absorbent, an antistatic agent, an antioxidant, a lubricating agent, a fire retardant, a pigment, a plasticizer and the like, may be used depending on necessity.

At this time, mixing is sufficiently effected under appropriate selection of the capacity of the mixer, the rotation speed of blades of the mixer, the mixing time and the like. Subsequently, the mixture is subjected to melt mixing by using a uniaxial or multiaxial screw extruder. The number of screws, the number of kneading screw zones, the cylinder temperature, the mixing speed and the like of the extruder are necessarily controlled with a controller to provide an appropriate resin temperature with reference to the physical property of the thermoplastic resin, and in order to obtain a sufficient mixed state, it is necessary that the various parameters, such as the number of screws, the mixing speed and the like, are comprehensively determined.

The mixture thus melt mixed is sufficiently cooled, and then pulverized by a known method, such as a ball mill, a sand mill, a hammer mill, a gas flow pulverizing method and the like. In the case where cooling cannot be sufficiently effected by the ordinary process, cooling or freezing pulverization method may be selected.

As other production processes, as described in the foregoing, the antibacterial composite particles can be produced by such a method as emulsion polymerization, suspension polymerization and the like, of a mixture of a monomer component of the polymer of the core base material with the calcium phosphate antibacterial agent.

For example, in the case of the emulsion polymerization, a monomer mixture containing the inorganic antibacterial agent and a polymerizable monomer is polymerized in an aqueous medium in the presence of an emulsifier and a water soluble polymerization initiator, whereby the antibacterial composite particles of the invention can be produced.

In alternative, the antibacterial composite particles of the invention can be produced by soap-free emulsion polymerization, in which no emulsifier is used.

Upon polymerizing the monomer component, a polymerization initiator may be used. As the polymerization initiator, the known polymerization initiators may be used. Examples thereof include hydrogen peroxide; a persulfate salt, such as sodium persulfate, ammonium persulfate, potassium persulfate and the like; an organic peroxide, such as benzoyl peroxide, lauroyl peroxide, caproyl peroxide, peracetic acid, t-butylhydroxy peroxide, methyl ethyl ketone peroxide, t-butyl perphthalate and the like; an azo compound, such as azobisisobutyronitrile, azobisisobutylamide and the like; and the like. These polymerization initiators may be used solely or may be used after mixing two or more kinds thereof.

Upon carrying out the polymerization, furthermore, a chain transfer agent, such as lauryl mercaptan, dodecyl mercaptan, 2-mercaptoethanol, 2-mercaptoacetic acid, carbon tetrachloride, carbon tetrabromide and the like, may be added to adjust the molecular weight of the resin thus obtained. These may be used solely or may be used after mixing two or more kinds thereof.

In the resin product of the invention, such as a molded article, fibers and the like, other additives that are generally used in a resin composition as a raw material of various kinds of resin products, such as an ultraviolet ray absorbent, an antistatic agent, an antioxidant, a lubricating agent, a fire retardant, a pigment, a plasticizer and the like, may be used depending on necessity, in addition to the aforementioned inorganic antibacterial agent.

The molding method for obtaining the antibacterial resin composition and the antibacterial resin product of the invention is not particularly limited, and the known techniques may be employed. For example, the antibacterial composite particles are melt mixed in a synthetic resin composition as the base material, and the mixture is subjected to the known molding method, such as extrusion molding, injection molding and the like, to obtain various kinds of resin molded articles, in which the inorganic antibacterial agent is uniformly dispersed in the synthetic resin composition to exert good antibacterial activity.

Upon producing antibacterial fibers, the antibacterial composite particles of the invention are mixed with the fiber forming polymer at an arbitrary stage until discharge of the fiber forming polymer from a spinning nozzle, followed by spinning, whereby fibers having sufficient antibacterial activity can be obtained without impairing the inherent characteristics of the material.

It is also possible that the antibacterial composite particles are again melted to form into fine particles, and then used in an molded article, or in alternative, they are melt mixed with the basic material resin in an appropriate concentration, followed by forming into fine particles, to form a compound or a master batch, and then the antibacterial resin composition, the antibacterial resin product, the antibacterial fibers and the like are produced.

As examples of specific purposes of the antibacterial resin composition of the invention, it can be used in various products, such as various kinds of packing materials, such as a packing film and the like, a filter for an air conditioner, a filter for a water cleaner, a food cutting board, an interior of a refrigerator, a medical appliance, various kinds of tubes, a packing, a container for foods and the like, and can impart good antibacterial activity with durability to those products. A filament yarn, a spun yarn, a woven or knitted fabric, a nonwoven fabric and the like can be produced from the antibacterial fibers of the invention, and they are utilized as clothing, such as an outer wear, an underwear, a working wear and the like, a sole insert, socks, a dustcloth, stockings, a toy, a paint, a coverlet, a bed, a carpet, a white coat, a patient wear, a surgical dressing, gauze, a toothbrush and the like.

BEST MODE FOR CARRYING OUT THE INVENTION

The invention will be specifically described with reference to the following examples and comparative examples, but the invention is not limited thereto.

[Antibacterial Composite Particles]

(1) Antibacterial Composite Particles of the Invention

PRODUCTION EXAMPLES 1 and 2

1. The polyester shown in Table 1 (composition: polycondensate of terephthalic acid and 2 mole polyoxyethylene adduct of bisphenol A, number average molecular weight: $5.2 \times 10^3$) was pulverized to prepare polyester particles having a volume average particle diameter of 100 μm.

2. 1.0 kg of tricalcium phosphate and 22 g of silver nitride were added to 10 L of distilled water, followed by stirring. Subsequently, the product thus formed was washed with distilled water and dried to obtain silver-carried tricalcium phosphate. Furthermore, the silver-carried tricalcium phosphate was baked at 800° C., pulverized, and classified with a sieve of 200 mesh by using a sieving machine, so as to prepare antibacterial tricalcium phosphate inorganic fine particles having about 1.3% of silver carried thereon. The antibacterial tricalcium phosphate inorganic fine particles had a volume average particle diameter of 0.3 μm.

3. The polyester particles and the antibacterial tricalcium phosphate inorganic fine particles in prescribed ratios (Table 1) were placed in a Henschel mixer, followed by subjecting high speed stirring, to obtain antibacterial composite particles of the invention (Production Examples 1 and 2).

(2) Antibacterial Composite Particles of the Invention

PRODUCTION EXAMPLE 3

The antibacterial composite particles of the invention (Production Example 3) were produced by a mixing and pulverizing method of the polyester shown in Table 1 (composition: polycondensate of terephthalic acid and 2 mole polyoxyethylene adduct of bisphenol A, number average molecular weight: $5.2 \times 10^3$) and the aforementioned antibacterial tricalcium phosphate inorganic fine particles at a mixing amount of 30% by weight based on the polymer. Specifically, the antibacterial tricalcium phosphate inorganic fine particles and the polyester were placed in a Henschel mixer and subjected to preliminary dispersion. Subsequently, it was melt mixed by using an extruder, and the resulting mixture was cooled and subjected to pulverization to make a volume average particle diameter of 100 μm, so as to obtain antibacterial composite particles of the invention (Production Example 3).

(3) Antibacterial Composite Particles of the Invention

PRODUCTION EXAMPLE 4

The antibacterial composite particles of the invention (Production Example 4) were produced by a mixing and pulverizing method of the styrene-n-butyl acrylate copolymer shown in Table 1 (St/Ac ratio: 90/10, number average molecular weight: $5.9 \times 10^3$, weight average molecular weight: peaks present at $6.0 \times 10^3$ and $6.0 \times 10^5$ on distribution) and the aforementioned antibacterial tricalcium phosphate inorganic fine particles. Specifically, the antibacterial tricalciumphosphate inorganic fine particles and the polymer were placed in a Henschel mixer and subjected to preliminary dispersion. Subsequently, it was melt mixed by using an extruder, and the resulting mixture was cooled and subjected to pulverization to make a volume average particle diameter of 100 μm, so as to obtain antibacterial composite particles of the invention (Production Example 4). The mixing ratio of the antibacterial agent was 20% by weight based on the polymer.

(4) Antibacterial Composite Particles of the Invention

PRODUCTION EXAMPLE 5

The antibacterial composite particles of the invention (Production Example 5) were produced by a mixing and pulverizing method of the styrene resin shown in Table 1 (number average molecular weight: $2.5 \times 10^4$) and the aforementioned antibacterial tricalcium phosphate inorganic fine particles. Specifically, the antibacterial tricalciumphosphate inorganic fine particles and the polymer were placed in a Henschel mixer and subjected to preliminary dispersion. Subsequently, it was melt mixed by using an extruder, and the resulting mixture was cooled and subjected to pulverization to make a volume average particle diameter of 100 μm, so as to obtain antibacterial composite particles of the invention (Production Example 5). The mixing ratio of the antibacterial agent was 10% by weight based on the polymer.

(5) Antibacterial Composite Particles of the Invention

PRODUCTION EXAMPLE 6

The oxidized polyethylene wax shown in Table 1 (number average molecular weight: $1.8 \times 10^3$) was pulverized to prepare resin particles having a volume average particle diameter of 100 μm, and then the antibacterial composite particles of the invention (Production Example 6) were produced by using the aforementioned antibacterial tricalcium phosphate inorganic fine particles. Specifically, the antibacterial tricalcium phosphate inorganic fine particles and the polymer were placed in a Henschel mixer and subjected to high speed stirring to obtain Production Example 6. The mixing ratio of the antibacterial agent was 10% by weight based on the polymer.

(6) Antibacterial Composite Particles of the Invention

PRODUCTION EXAMPLE 7

The polystyrene resin shown in Table 1 (number average molecular weight: $1.8 \times 10^5$) was pulverized to prepare resin particles having a volume average particle diameter of 100 μm, and then the antibacterial composite particles of the invention (Production Example 7) were produced by using the aforementioned antibacterial tricalcium phosphate inorganic fine particles. Specifically, the antibacterial tricalciumphosphate inorganic fine particles and the polymer were placed in a Henschel mixer and subjected to high speed stirring to obtain Production Example 7. The mixing ratio of the antibacterial agent was 10% by weight based on the polymer.

TABLE 1

Amount of Antibacterial Agent (wt %) contained in Antibacterial Composite Particles and Physical Properties of Resin Particles

|  | Production Example 1 | Production Example 2 | Production Example 3 | Production Example 4 | Production Example 5 | Production Example 6 | Production Example 7 |
|---|---|---|---|---|---|---|---|
| Amount of antibacterial agent (wt %) | 4.0 | 10.0 | 30.0 | 20.0 | 10.0 | 10.0 | 10.0 |
| Tg (° C.) | 60 | 60 | 60 | 67 | 98 | none | 102 |
| $\eta^*$ (90° C.) (Pa · S) | $3.1 \times 10^4$ | $3.7 \times 10^4$ | $6.0 \times 10^4$ | $3.0 \times 10^5$ | $1.5 \times 10^9$ | $2.0 \times 10^{-1}$ | $1.6 \times 10^9$ |
| $\eta^*$ (100° C.) (Pa · S) | $7.0 \times 10^3$ | $8.0 \times 10^4$ | $1.5 \times 10^4$ | $7.5 \times 10^4$ | $6.0 \times 10^8$ | $1.8 \times 10^{-1}$ | $6.8 \times 10^8$ |
| $\eta^*$ (180° C.) (Pa · S) | $2.1 \times 10^1$ | $2.5 \times 10^1$ | $5.0 \times 10^1$ | $3.0 \times 10^3$ | $8.0 \times 10^2$ | $1.0 \times 10^{-1}$ | $1.5 \times 10^5$ |
| Softening point (° C.) | 98 | 99 | 103 | 138 | 155 | 85 | 235 |
| Mw | $1.8 \times 10^4$ | $1.8 \times 10^4$ | $1.8 \times 10^4$ | $2.7 \times 10^5$ | $5.5 \times 10^4$ | $5.0 \times 10^3$ | $4.5 \times 10^5$ |

$\eta^*$ represents a complex viscosity.

[Measurement of Physical Properties of Antibacterial Composite Particles]

Production Examples 1 to 7 were subjected to measurement of physical properties as follows.

The glass transition temperature was measured by using a differential scanning calorimeter (DSC-50, produced by Shimadzu Corp.) at a temperature increasing rate of 10° C. per min.

The melt viscosity at 90° C. η* (90° C.), the melt viscosity at 100° C. η* (100° C.) and the melt viscosity at 180° C. η* (180° C.) of Production Examples 1 to 7 were measured with the ARES measuring device produced by Rheometric Scientific, Inc., as described in the foregoing.

The softening point was measured by using a flow tester Model CFT-500F (produced by Shimadzu Corp.) using a die having a diameter of 1.0 mm and a length of 1 mm under conditions of a load of 10 kgf and a sample amount of 1.0 g, with a temperature at a melt viscosity of $1 \times 10^4$ Pa·S on the viscosity curve being designated as the softening point. The weight average molecular weight was measured by using a molecular weight measuring machine (HLC-8120, produced by Tosoh Corp.) with polystyrene as a standard polymer.

[Production of Antibacterial Resin Molded Article]

As antibacterial resin molded articles using the antibacterial composite particles of Production Examples 1 to 7, they were added to a polypropylene resin as a base material (softening point: 140° C., weight average molecular weight: $2.25 \times 10^5$) in the amount shown in the table, and antibacterial resin plates were produced with a melt mixing extrusion molding machine.

(Table 2)

[Production of Antibacterial Preliminary Twisted Fibers (1)]

Various kinds of antibacterial preliminary twisted fibers were produced by using the antibacterial composite particles of Production Examples 1 to 7. Specifically, 5% by weight of the antibacterial composite particles of Production Examples 1 to 7 were added to polyethylene terephthalate as a base resin for forming fibers (softening point: 240° C., weight average molecular weight Mw: 140,000), and it was subjected to melt spinning by an ordinary method at a winding speed of 1,200 m/min to obtain the various kinds of antibacterial preliminary twisted fibers with a spindle type drawing preliminary twisting machine (Table 3).

[Production of Antibacterial Preliminary Twisted Fibers (2)]

A monomer mixture containing 96% by weight of acrylonitrile and 4% by weight of vinyl acetate was subjected to aqueous suspension polymerization with ammonium persulfate as an initiator to produce a polyacrylonitrile polymer having a weight average molecular weight of $20 \times 10^4$. The resulting polymer was dissolved in dimethyformamide, and 5% by weight of the antibacterial composite particles of Production Examples 1 to 7 were added to the resulting polymer stock solution to prepare spinning stock solutions having a polymer concentration of 20%.

The spinning stock solution was ejected from a nozzle by the wet spinningmethod, and coagulated inadimethylformamide aqueous solution, followed by washing with water to remove dimethylformamide. Thereafter, it was drawn twice under wet heating at 100° C. and then dried with a heater roller at 120° C. The fibers thus dried were applied to a heating roller having a surface temperature set at 170° C. to be drawn twice under dry heating, and then they were applied with an oily agent and wound on a heating roller, so as to produce antibacterial preliminary twisted fibers (Table 4).

The difference in softening point referred below is a value obtained by subtracting the softening point of the composite resin from the softening point of the basic material resin.

TABLE 2

Polypropylene Softening point: 140° C.

| | Example 1 | Example 2 | Example 3 | Example 4 | Example 5 | Comparative Example 1 | Comparative Example 2 | Comparative Example 3 |
|---|---|---|---|---|---|---|---|---|
| Composite particles used | Production Example 1 | Production Example 2 | Production Example 3 | Production Example 3 | Production Example 4 | Production Example 5 | Production Example 6 | Production Example 7 |
| Addition amount of composite particles | 2.5 wt % | 1.5 wt % | 1.0 wt % | 1.7 wt % | 1.25 wt % | 5.0 wt % | 5.0 wt % | 5.0 wt % |
| Difference in softening point (° C.) | 42 | 41 | 37 | 37 | 2 | −15 | 55 | −95 |

TABLE 3

PET Softening point: 240° C.

| | Example 1 | Example 2 | Example 3 | Example 4 | Comparative Example 1 | Comparative Example 2 | Comparative Example 3 |
|---|---|---|---|---|---|---|---|
| Composite particles used | Production Example 1 | Production Example 2 | Production Example 3 | Production Example 4 | Production Example 5 | Production Example 6 | Production Example 7 |
| Addition amount of composite particles | 2.5 wt % | 2.0 wt % | 0.7 wt % | 1.0 wt % | 2.5 wt % | 2.5 wt % | 2.5 wt % |
| Difference in softening point (° C.) | 142 | 141 | 137 | 102 | 85 | 155 | 5 |

TABLE 4

| | Example 1 | Example 2 | Example 3 | Example 4 | Comparative Example 1 | Comparative Example 2 | Comparative Example 3 |
|---|---|---|---|---|---|---|---|
| Acrylic resin Softening point: 150° C. | | | | | | | |
| Composite particles used | Production Example 1 | Production Example 2 | Production Example 3 | Production Example 4 | Production Example 5 | Production Example 6 | Production Example 7 |
| Addition amount of composite particles | 2.5 wt % | 2.0 wt % | 1.0 wt % | 2.0 wt % | 5.0 wt % | 5.0 wt % | 5.0 wt % |
| Difference in softening point (° C.) | 52 | 51 | 47 | 12 | −5 | 65 | −85 |

(1) Antibacterial Activity Test

The antibacterial resin plates and the antibacterial preliminary twisted fibers produced as in the foregoing were subjected to the following antibacterial activity test.

1. Antibacterial Resin Plate

An antibacterial activity test was carried out according to the antibacterial activity test method for an antibacterial processed product JIS Z 2801.

The plate molded articles (thickness: 2 mm) of the antibacterial resin plates of Examples 1 to 5 and Comparative Examples 1 to 3 were cut into 50 mm×50 mm, and the surface of the molded article was wiped with gauze impregnated with ethanol. The plates were allowed to stand under an atmosphere of 23° C. and 60% RH for 24 hours and then designated as test pieces for antibacterial activity. The test pieces were inoculated with 0.4 mL of a bacterial suspension, and after attaching a polyethylene film of 45 mm×45 mm thereto, they were stored at 37° C. The survived bacteria were eluted with a SCDLP culture medium (produced by Nihon Pharmaceutical Co., Ltd.) at the start of the storage and after 24 hours. The eluted solution was measured for the number of survived bacteria by the agar plate culturing method (at 37° C. for 24 hours) by using a standard agar medium for measuring number of bacterial (produced by Nissui Corp.), so as to convert to the number of survived bacterial per one test piece.

*Bacillus coli* (IFO 3972) was used as the test bacteria. In order to prepare the test bacterial suspension, an ordinary bouillon culture medium was prepared by dissolving 5 mg of meat extract, 10 mg of peptone and 5 mg of sodium chloride in 1 L of distilled water. A solution was prepared by further diluting the bouillon culture medium with distilled water by 500 times, in which the *Bacillus coli* was suspended to adjust the number of bacteria to $10^6$ per 1 mL. The results of the antibacterial activity test are shown in Table 5.

TABLE 5

| | Example 1 | Example 2 | Example 3 | Example 4 | Example 5 | Comparative Example 1 | Comparative Example 2 | Comparative Example 3 |
|---|---|---|---|---|---|---|---|---|
| Polypropylene antibacterial plate softening point: 140° C. | | | | | | | | |
| Content of antibacterial agent (wt %) | 0.1 | 0.15 | 0.3 | 0.51 | 0.25 | 0.5 | 0.5 | 0.5 |
| Number of survived bacteria | 350 | <10 | <10 | <10 | $8.7 \times 10^4$ | $7.9 \times 10^5$ | $4.7 \times 10^6$ | $6.1 \times 10^6$ |

2. Antibacterial Preliminary Twisted Fibers

An antibacterial activity test was carried out according to the antibacterial activity test method for a fiber product JIS L 1902.

Specifically, a bacterial suspension of the following test bacteria of $1.3 \times 10^5$ per mL was prepared with sterilized Nutrient Broth of 1/20 concentration, and 0.4 g each of the samples of Examples 1 to 4 and Comparative Examples 1 to 3 were inoculated with 0.2 mL of the bacterial suspension, followed by cultivated at 37° C. for 18 hours. After completing cultivation, the test bacteria were eluted, and the eluted liquid was cultivated by a mixed agar plate culturing method at 37° C. for 24 to 48 hours to measure the number of survived bacteria. *Staphylococcus aureus* ATTC 6538P was used as the test bacteria. The results of the antibacterial test are shown in Tables 6 and 7.

TABLE 6

PET fibers Softening point: 240° C.

|  | Example 1 | Example 2 | Example 3 | Example 4 | Comparative Example 1 | Comparative Example 2 | Comparative Example 3 |
|---|---|---|---|---|---|---|---|
| Content of antibacterial agent (wt %) | 0.1 | 0.2 | 0.21 | 0.2 | 0.25 | 0.25 | 0.25 |
| Number of survived bacteria | 830 | <20 | <20 | $4.5 \times 10^3$ | $4.5 \times 10^5$ | $1.2 \times 10^6$ | $8.7 \times 10^5$ |

TABLE 7

Acrylic resin fibers Softening point: 240° C.

|  | Example 1 | Example 2 | Example 3 | Example 4 | Comparative Example 1 | Comparative Example 2 | Comparative Example 3 |
|---|---|---|---|---|---|---|---|
| Content of antibacterial agent (wt %) | 0.1 | 0.2 | 0.3 | 0.4 | 0.5 | 0.5 | 0.5 |
| Number of survived bacteria | 640 | <20 | <20 | $3.5 \times 10^3$ | $8.5 \times 10^4$ | $1.5 \times 10^5$ | $4.0 \times 10^5$ |

It is understood from the results shown in the aforementioned examples that the antibacterial resin molded articles and the antibacterial fibers of the examples exhibit sufficiently high antibacterial activity even with the same mixing amount of the inorganic antibacterial agent. It is understood that those produced by using the antibacterial composite particles of the comparative examples, on the other hand, are significantly low in antibacterial activity even though the antibacterial agent is mixed in an amount equal to of larger than those using the antibacterial composite particles of the invention.

It is understood from the comparison of the antibacterial tests of Example 5 of the antibacterial resin plate, Example 4 of the antibacterial PET fibers and Example 4 of the antibacterial acrylic resin fibers (Tables 5 to 7) that these are produced by using the antibacterial composite particles of the invention (Example 4) and have certain antibacterial activity, but the antibacterial activity is lowered in the case where such a basic material resin is used that has a difference in softening point from the resin particles constituting the antibacterial composite particles of less than 20° C.

INDUSTRIAL APPLICABILITY

As described in the foregoing, the antibacterial composite particles of the invention are constituted by the polymer base material having the particular glass transition point and melt viscosity and the fine particles of the inorganic antibacterial agent, whereby they have good dispersibility to the base material constituting the synthetic resin product to provide various kinds of synthetic resin molded articles having good antibacterial activity. In the case where antibacterial fibers are produced by using the antibacterial composite particles of the invention, fibers having sufficient antibacterial activity can be obtained without impairing the inherent characteristics of the material.

The invention claimed is:

1. Antibacterial composite particles comprising a thermoplastic polymer base material and fine particles of a calcium phosphate compound, wherein the thermoplastic polymer base material has a melt viscosity satisfying the following equation (1) and a glass transition temperature of from 10 to 85° C., said fine particles of a calcium phosphate compound having an antibacterial metal carried thereon:

$$10^4 \text{Pa·S} \leq \eta^*(90° \text{C.}) \leq 10^6 \text{Pa·S} \quad (1)$$

wherein $\eta^*$ represents a complex viscosity.

2. Antibacterial composite particles as claimed in claim 1, wherein the thermoplastic polymer base material has a melt viscosity satisfying the following equation (2):

$$10^3 Pa \cdot S \leq \eta^*(100^\circ C.) \leq 10^5 Pa \cdot S \quad (2)$$

wherein η* represents a complex viscosity.

3. Antibacterial composite particles as claimed in claim 1, wherein the melt viscosity of the thermoplastic polymer base material satisfies the following equation (3):

$$10^0 Pa \cdot S \leq \eta^*(180^\circ C.) \leq 10^3 Pa \cdot S \quad (3)$$

wherein η* represents a complex viscosity.

4. Antibacterial composite particles as claimed in claim 1, wherein the thermoplastic polymer base material has a softening point of from 50 to 150° C.

5. Antibacterial composite particles as claimed in claim 1, wherein the thermoplastic polymer base material has a weight average molecular weight of from 1,000 to 100,000.

6. Antibacterial composite particles as claimed in claim 1, wherein the antibacterial metal is at least one metal selected from silver, copper and zinc.

7. Antibacterial composite particles as claimed in claim 1, wherein the antibacterial metal is present in an amount of from 0.05 to 30.0% by weight based on the fine particles of calcium phosphate compound.

8. Antibacterial composite particles as claimed in claim 1, wherein the fine particles of calcium phosphate compound are present in an amount of from 0.1 to 60.0% by weight based on the thermoplastic polymer base material.

9. Antibacterial composite particles as claimed in claim 1, wherein the thermoplastic polymer base material is a non-crystalline polymer having a glass transition temperature of from 40 to 80° C.

10. Antibacterial composite particles as claimed in claim 1, wherein the thermoplastic polymer base material is selected from polystyrene, polyester, polyamide, polyolefin, an acrylic resin and copolymers thereof.

11. Antibacterial composite particles as claimed in claim 1, wherein the antibacterial composite particles have a volume average particle diameter of from 1 to 2,000 µm.

12. Antibacterial composite particles as claimed in claim 1, wherein the fine particles of calcium phosphate compound have a volume average particle diameter of 10 µm or less.

13. An antibacterial resin composition comprising a basic material resin having the antibacterial composite particles as claimed in claim 1 dispersed therein.

14. An antibacterial resin composition as claimed in claim 13, wherein the antibacterial composite particles have a dispersed amount of from 0.1 to 60.0% by weight based on the basic material resin.

15. An antibacterial resin composition as claimed in claim 13, wherein the fine particles of calcium phosphate compound are present in an amount of from 0.01 to 10.0% by weight based on the basic material resin.

16. An antibacterial resin composition as claimed in claim 13, wherein the thermoplastic polymer base material is present in an amount of from 0.1 to 60.0% by weight based on the basic material resin.

17. An antibacterial resin composition as claimed in claim 13, wherein the thermoplastic polymer base material and the basic material resin are selected from a combination consisting of polyester/polyester, polyester/polyolefin, polyester/polyamide, polyester/acryl, polyolefin/polyolefin, polyamide/polyamide, acryl/styrene, acryl/acryl, styrene/acryl and styrene/styrene.

18. An antibacterial resin product formed with the antibacterial resin composition as claimed in claim 13.

19. An antibacterial resin product as claimed in claim 18, wherein the antibacterial resin product is selected from a film, a sheet and fibers.

20. An antibacterial resin composition as claimed in claim 13, wherein the basic material resin has a softening point at least 20° C. higher than a softening point of the thermoplastic polymer base material.

* * * * *